(12) United States Patent
Stiger

(10) Patent No.: US 8,920,481 B2
(45) Date of Patent: Dec. 30, 2014

(54) ENDOVASCULAR DELIVERY SYSTEM HAVING TEXTILE COMPONENT FOR IMPLANT RESTRAINT AND DELIVERY

(75) Inventor: Mark Stiger, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 578 days.

(21) Appl. No.: 12/426,431

(22) Filed: Apr. 20, 2009

(65) Prior Publication Data

US 2010/0268328 A1    Oct. 21, 2010

(51) Int. Cl.
*A61F 2/06* (2013.01)
*A61F 2/966* (2013.01)
*A61F 2/95* (2013.01)

(52) U.S. Cl.
CPC . *A61F 2/966* (2013.01); *A61F 2/95* (2013.01); *A61F 2/007* (2013.01)
USPC ........................................................ 623/1.11

(58) Field of Classification Search
CPC ........... A61F 2/95; A61F 2/954; A61F 2/962; A61F 2/966; A61F 2002/95; A61F 2002/962; A61F 2002/966
USPC .......... 623/1.11, 1.12; 606/108; 604/104, 107
See application file for complete search history.

(56) References Cited

U.S. PATENT DOCUMENTS

| | | | |
|---|---|---|---|
| 5,709,703 A * | 1/1998 | Lukic et al. | 623/1.12 |
| 5,824,041 A | 10/1998 | Lenker et al. | |
| 6,254,609 B1 | 7/2001 | Vrba et al. | |
| 6,315,792 B1 | 11/2001 | Armstrong et al. | |
| 6,945,990 B2 | 9/2005 | Greenan | |
| 2002/0099431 A1 | 7/2002 | Armstrong et al. | |
| 2003/0004561 A1 | 1/2003 | Bigus et al. | |
| 2003/0105453 A1* | 6/2003 | Stewart et al. | 604/537 |
| 2006/0100687 A1* | 5/2006 | Fahey et al. | 623/1.11 |
| 2006/0247757 A1* | 11/2006 | Kaufmann et al. | 623/1.12 |
| 2007/0219612 A1* | 9/2007 | Andreas et al. | 623/1.11 |

* cited by examiner

*Primary Examiner* — Thomas McEvoy

(57) ABSTRACT

A stent-graft delivery system is disclosed having an outer tubular shaft or sheath with a relatively stiff proximal segment and a distal segment formed from a tubular textile component. The proximal segment being formed from a polymeric tubing and having a distal end attached to a proximal end of the tubular textile component. During tracking of the delivery system through the vasculature, a self-expanding stent-graft is constrained by and within the tubular textile component in a compressed delivery configuration. Upon positioning at a treatment site, such as an aneurysm, retraction of the outer tubular shaft proximally slides the tubular textile component over the stent-graft to expose and deploy the stent-graft. The tubular textile component may be made from strands of one or more biocompatible materials that have been formed into a textile by weaving, braiding, knitting, crocheting, felting or a combination thereof.

12 Claims, 3 Drawing Sheets

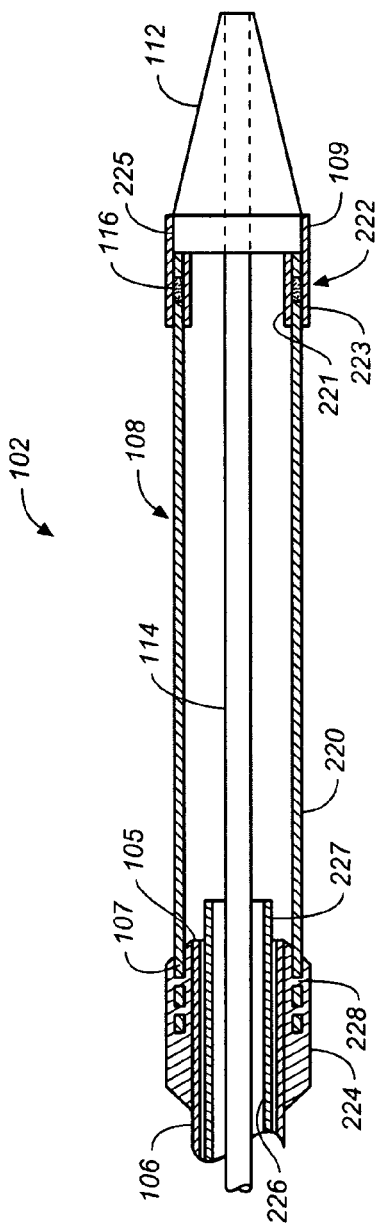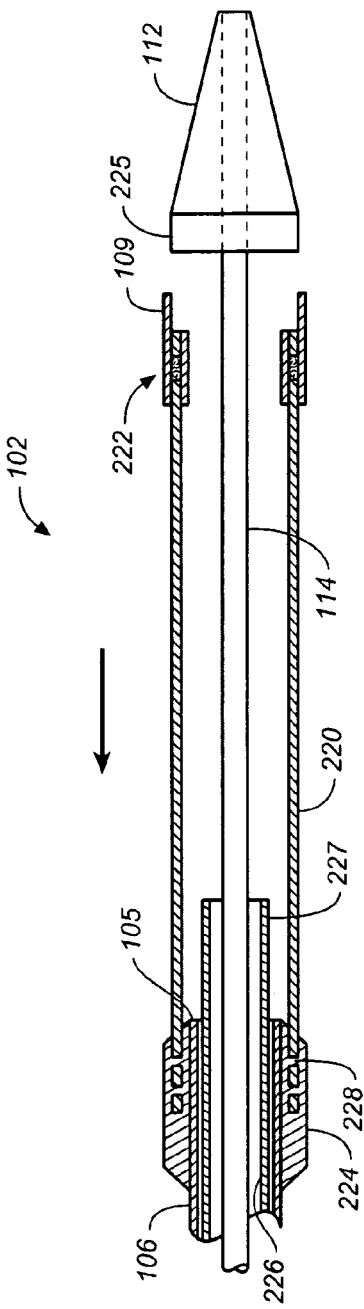

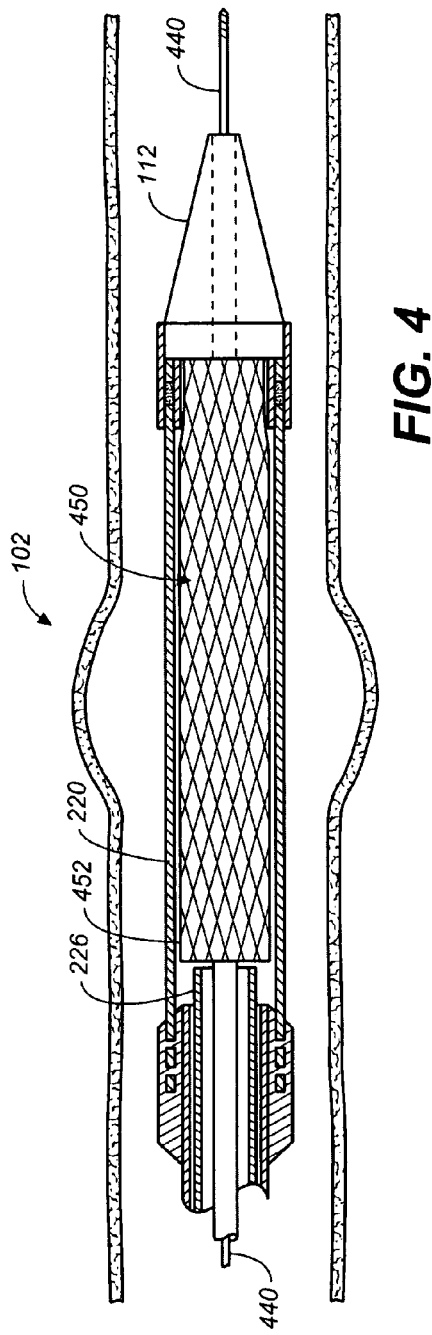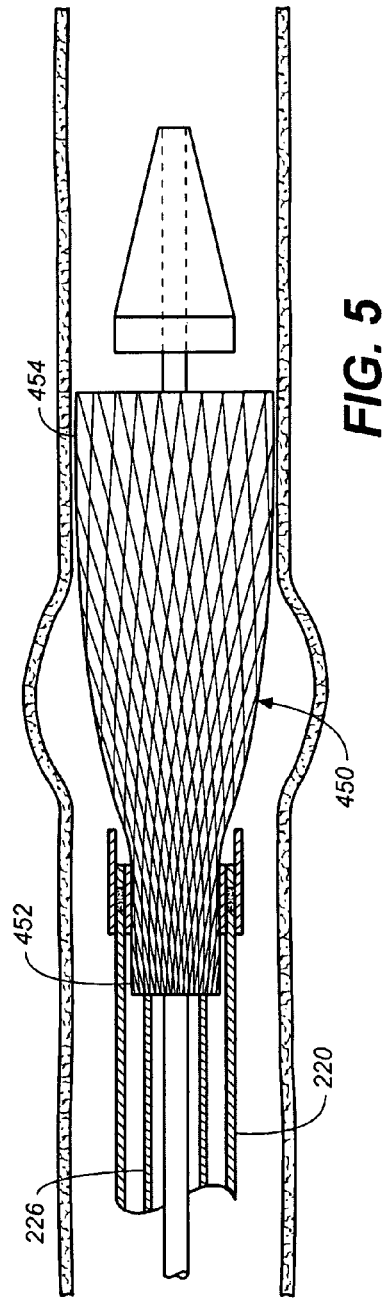

ENDOVASCULAR DELIVERY SYSTEM HAVING TEXTILE COMPONENT FOR IMPLANT RESTRAINT AND DELIVERY

FIELD OF THE INVENTION

The invention relates generally to medical devices and procedures, and more particularly to an endovascular delivery system for deploying a stent-graft in a vascular system.

BACKGROUND

Prostheses for implantation in blood vessels or other similar organs of the living body are, in general, well known in the medical art. For example, prosthetic vascular grafts constructed of biocompatible materials, such as DACRON material or expanded, porous polytetrafluoroethylene (ePTFE) tubing, have been employed to replace or bypass damaged or occluded natural blood vessels. A tubular graft material supported by framework is known as a stent-graft or an endoluminal/endovascular graft. In general, endovascularly delivered stent-grafts typically have framework that includes at least one graft anchoring component that operates to hold the tubular graft in its intended position within the blood vessel. Most commonly, the graft anchoring component is one or more radially compressible stents that are radially expanded in vivo to anchor the tubular graft to the wall of a blood vessel or anatomical conduit. Thus, endovascular grafts are typically held in place by mechanical engagement and friction due to the apposition forces provided by the expandable stents. In general, the use of stent-grafts for treatment or isolation of vascular aneurysms and vessel walls, which have been thinned or thickened by disease (endoluminal repair or exclusion), are well known.

In general, rather than performing an open surgical procedure to implant a graft that may be traumatic and invasive, endovascular grafts or stent-grafts are preferably deployed through a less invasive intraluminal delivery. These stent-grafts may include either self-expanding or balloon-expandable stent structures with a tubular graft component attached to the stent structure. The stent-graft can be reduced in diameter, by crimping onto a balloon catheter or by being contained within a sheath component of a delivery catheter, and advanced through the venous or arterial vasculature. More particularly, a lumen of the vasculature is accessed at a convenient and low trauma entry point, and the compressed or crimped stent-graft is routed through the vasculature to the site where the prosthesis is to be deployed. Once the stent-graft is positioned at a treatment site, the stent structure may be radially expanded or allowed to radially expand so that at least a portion of it contacts and substantially conforms to a portion of the surrounding interior wall of the lumen, e.g., the blood vessel wall or in another application an anatomical conduit, to hold the graft component firmly in place.

More particularly, intraluminal deployment of a self-expanding stent-graft is typically effected using a delivery catheter with coaxial inner (plunger) and outer tubular members arranged for relative axial movement. The stent-graft is compressed and disposed within a distal end of the outer tubular member in front of or distal to the inner tubular member. The delivery catheter is then maneuvered, typically routed though a lumen, e.g., vessel, until the distal end of the catheter with the stent-graft compressed therein is positioned at the intended treatment site. The inner tubular member is then held stationary to prevent proximal movement of the stent-graft while the outer tubular member of the delivery catheter is proximally withdrawn. As the outer tubular member is withdrawn, the stent-graft radially expands so that at least a portion comes into substantially conforming surface contact with a portion of the interior of the lumen, e.g., blood vessel wall.

Many current commercial and clinical stent-graft delivery systems employ a relatively stiff outer member, or catheter shaft, to restrain the stent or stent-graft during introduction and tracking to an intravascular treatment site. The stiffness of such a catheter shaft, when combined with a relatively stiff guidewire, may straighten the patient's anatomy and thus increase the chance of vessel trauma during the procedure. Some manufacturers have addressed the stiffness of these devices by incorporating a textile, or flexible, catheter segment within the delivery system. The more flexible catheter segments are conventionally contained inside the stiffer, outer catheter shaft, which is employed during introduction and tracking of the catheter to the anatomy in the vicinity of the intravascular treatment site. Once so positioned the stiffer outer catheter shaft is withdrawn to expose the underlying flexible catheter segment, which is then maneuvered and positioned within the treatment site and subsequently retracted, or otherwise removed from constraining the stent-graft. Delivery devices having the afore-mentioned configuration do not address the potential trauma caused by introduction and tracking of the catheter devices prior to exposure of the flexible catheter segment and require a two-step delivery process.

Thus, those of skill in the art seek improvements in providing an endovascular stent-graft delivery system that exhibits improved flexibility without the bulkiness and larger crossing profile of a double sheath delivery system, and that may be introduced and tracked through the vasculature with minimal trauma. Embodiments of a stent-graft delivery system are described herein that improve flexibility by incorporating a textile segment as a distal outer shaft portion of the delivery system to lessen the effects of introducing and tracking the delivery system to the desired intravascular treatment site.

SUMMARY OF THE INVENTION

A stent-graft delivery system is disclosed having an outer tubular shaft or sheath with a relatively stiff proximal segment having a distal segment formed from a noncompliant tubular textile component for flexibility. The proximal segment being formed from a polymeric tubing and having a distal end attached, e.g., by an adhesive or a thermal bond, to a proximal end of the tubular textile component. A distal end of the tubular textile component includes a polymeric hub component attached, e.g., by an adhesive or a thermal bond, to provide radial support thereto. During tracking of the delivery system through the vasculature, a self-expanding stent-graft is constrained by and within the tubular textile component in a compressed delivery configuration. Upon positioning at a treatment site, such as an aneurysm, retraction of the outer tubular shaft proximally slides the tubular textile component over the stent-graft to expose and deploy the stent-graft. The tubular textile component may be made from strands of one or more biocompatible materials that have been formed into a textile by weaving, braiding, knitting, crocheting, felting or a combination thereof.

The delivery system may further include a tubular middle member disposed within the outer tubular shaft with a distal end positioned proximate a distal end of the stent-graft held within the tubular textile component. An inner shaft is concentrically disposed within the outer tubular shaft and the middle member and extends through the stent-graft to a flexible tip component, wherein the tip component is positioned at a proximal end of the stent-graft held within the tubular textile component. The outer tubular shaft is longitudinally slidable relative to the middle member, the inner shaft, and the tip component during retraction thereof and deployment of the stent-graft. The middle member acts as a proximal stop to prevent proximal movement of the stent-graft with the tubular textile component during retraction of the outer tubular shaft.

BRIEF DESCRIPTION OF DRAWINGS

The foregoing and other features and advantages of embodiments will be apparent from the following description as illustrated in the accompanying drawings. The accompanying drawings, which are incorporated herein and form a part of the specification, further serve to explain the principles of the embodiments and to enable a person skilled in the pertinent art to make and use the described embodiments herein. The drawings are not to scale.

FIG. 2 is a sectional view of the distal portion of the delivery system shown in FIG. 1 in a delivery configuration.

FIG. 3 is the distal portion shown in FIG. 2 in a deployment configuration.

FIG. 4 is a schematic sectional view of the distal portion of the delivery system shown in FIG. 1 spanning a vascular aneurysm with a stent-graft contained therein in a delivery configuration.

FIG. 5 is the distal portion shown in FIG. 4 with the stent-graft being deployed across the aneurysm.

DETAILED DESCRIPTION

Figure 1:
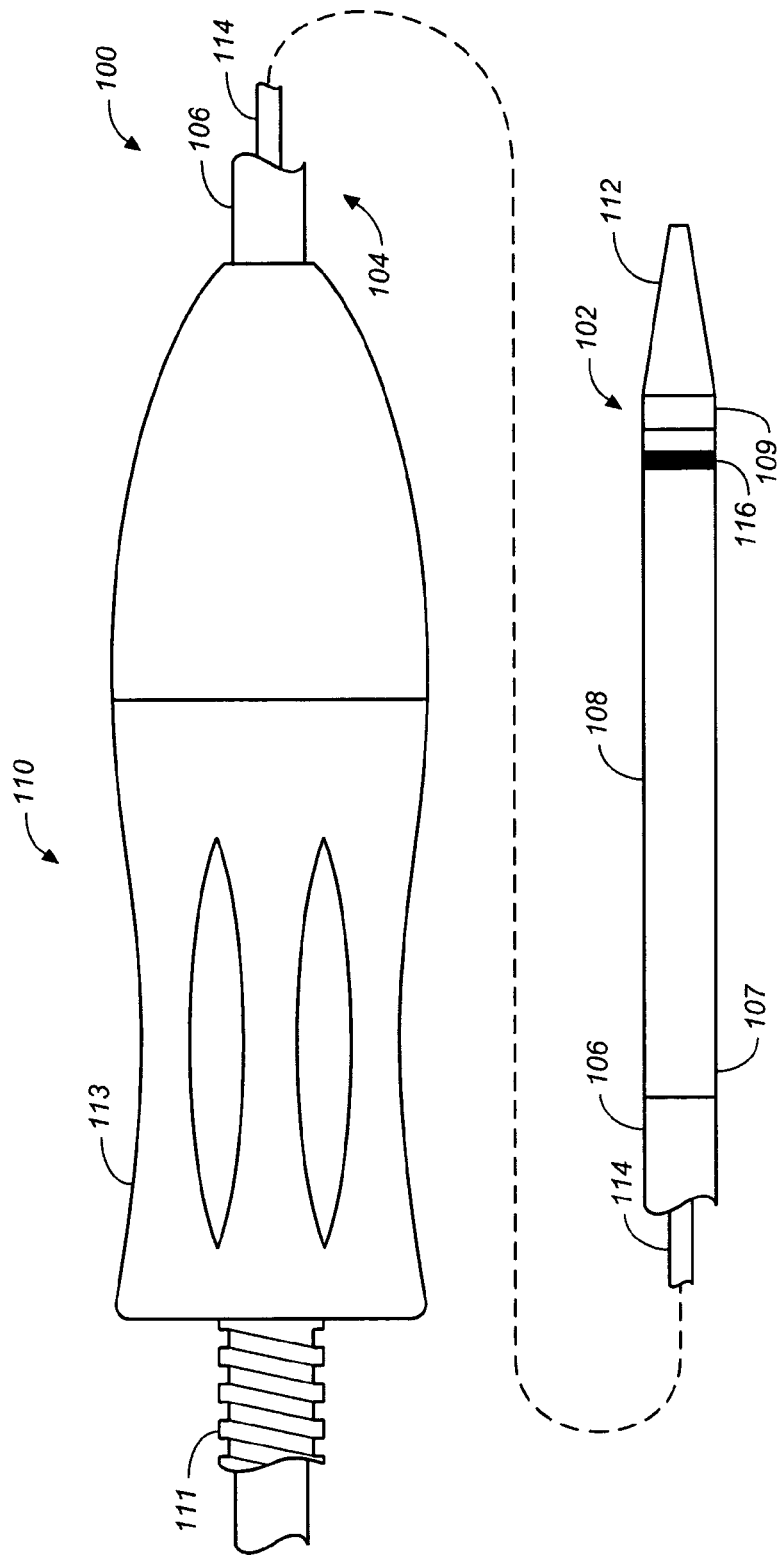
FIG. 1 is a schematic plan view of a stent-graft delivery system in accordance with an embodiment hereof with a distal portion shown enlarged.

Specific embodiments according to the present invention are now described with reference to the figures, wherein like reference numbers indicate identical or functionally similar elements. Unless otherwise indicated, in the following description, the terms "distal" and "proximal" are used with respect to a position or direction relative to the treating clinician. "Distal" and "distally" are positions distant from or in a direction away from the clinician, and "proximal" and "proximally" are positions near or in a direction toward the clinician.

The following detailed description is merely exemplary in nature. Although the description is in the context of treatment of blood vessels such as the coronary, carotid and renal arteries, the embodiments may also be used in any other body passageways where they are deemed useful.

FIG. 1 is a schematic plan view of a stent-graft delivery system 100 in accordance with an embodiment hereof with a distal portion 102 shown enlarged to better show the detail thereof. Delivery system 100 includes an outer tubular shaft or sheath 104 that is operably coupled to a deployment or control handle 110 at a proximal end of delivery system 100, which is positioned outside of the patient to be manipulated by a clinician. Control handle 110 includes a screwgear 111 and a slider assembly 113 that transmit a longitudinal retraction force to outer tubular shaft 104 when slider assembly 113 is rotated about an axis of delivery system 100 by the clinician, (see for example Medtronic's Xcelerant® Delivery System). In this manner controlled deployment of a stent-graft or other prosthesis may be achieved. The subsequent use of "stent-graft" herein should be understood to include other forms of endovascular prosthesis. Outer tubular shaft 104 extends to a tapered tip component 112 at a distal end of delivery system 100 and is longitudinally slidable relative thereto during deployment of a stent-graft as will be explained in detail below. Tip component 112 is a molded piece of PEBAX 4033 blended with barium sulfate to provide a flexible lubricious tip that is radiopaque.

Delivery system 100 has an over-the-wire catheter configuration and includes a guidewire shaft 114, which defines a lumen for receiving a guidewire, that extends from tip component 112 through outer tubular shaft 104 and handle 110 for substantially an entire length of delivery system 100. Guidewire shaft 114 may be made of polyethylene tubing or other flexible tubing.

Outer tubular shaft 104 has a proximal shaft segment 106 and a distal shaft segment 108. Proximal shaft segment 106 extends from handle 110 to a proximal end 107 of distal shaft segment 108 and is formed from tubing made of a semi-rigid material, such as polyether block amide, such as PEBAX®, polyamide, nylon or nylon blends, such as VESTAMID®, to provide sufficient stiffness and column strength to delivery system 100 for tracking through tortuous vessels. Distal shaft segment 108 has a distal end 109 that slides over and abuts tapered tip component 112 and is more flexible than proximal shaft segment 106 to allow delivery system 100 to be tracked through the vasculature while minimizing trauma. To maintain a suitable low-profile, outer tubular shaft 104 has a substantially constant outer diameter from a proximal end (not shown) of proximal shaft segment 106 to distal end 109 of distal shaft segment 108.

FIGS. 2 and 3 are sectional views of distal portion 102 of delivery system 100 that show the components of distal shaft segment 108 and the manner in which proximal end 107 of distal shaft segment 108 is attached to proximal shaft segment 106. Distal shaft segment 108 is substantially formed by a tubular textile component 220 that covers and restrains a self-expanding stent-graft in a compressed, delivery configuration as delivery system 100 is tracked through the vasculature. Textile component 220 is formed to be a non-compliant tubular structure, i.e., other than having surface irregularities from the textile component's conformance to the compressed stent-graft therein textile component 220 has a substantially constant outer diameter that does not change during loading, tracking or deployment of the self-expanding stent-graft.

Textile component 220 is a textile, i.e., fabric or cloth, to provide increased flexibility to distal portion 102 of delivery system 100. The textile is one or more biocompatible materials, e.g., polyester, polypropylene, polyethylene, ultra high molecular weight polyethylene, such as DYNEEMA®, or nitinol, strands of which may be formed into a textile tube by weaving, braiding, knitting, crocheting, felting or a combination thereof. Strands of the textile may be in a native monofilament form, or may include a number of filaments (multi-filament) twisted to form a strand of yarn. Textile component 220 is made from 40D polyester yarn woven into a textile tube that is designed to constrain and maintain a self-expanding stent-graft in a compressed, delivery configuration. The tubular textile component 220 is formed from a non-porous textile that will allow fluid to penetrate or seep through a surface thereof, i.e., is permeable. In an embodiment, textile component 220 has a wall thickness of 0.004 inch and a length of approximately 195 mm+/−20 mm.

Distal shaft segment 108 includes a hub component 222 attached to a distal end of tubular textile component 220 that has an inner diameter to tightly slide over a proximal end/portion 225 of tip component 112 in a frictional fit and a length, e.g., 10 mm, that covers a distal end of a constrained stent-graft, which may be a bare spring distal anchor of the stent-graft. Hub component 222 provides longitudinal stability and support to textile component 220 as delivery system 100 is tracked through the vasculature. Hub component 222 also radial supports the distal end of textile component 220 and eases retraction of textile component 220 over the distal end/anchor of the constrained stent-graft as described further below. Hub component 222 includes inner and outer support tubes 221, 223 that sandwich therebetween the distal end of tubular textile component 220 and a radiopaque marker band 116. Inner and outer support tubes 221, 223 are thermally bonded together and may be formed from short sections of polymeric tubing made of an elastomeric material, such as PEBAX®, or a nylon/nylon blend. The distal end of textile component 220 includes perforations (not shown for clarity) regularly spaced about a circumference to allow segments of inner and outer support tubes 221, 223 to thermally join therethrough during the thermal bonding process. In another embodiment, inner and outer support tubes 221, 223 may be attached to each other and/or textile component 220 with an adhesive, such as cyanoacrylate, which is also applied within the perforations to aid in adhesive attachment of inner support tube 221 to outer support tube 223 with textile component 220 therebetween.

A proximal end of textile component 220 is attached in a similar manner to a distal end of proximal shaft segment 106. As shown in FIGS. 2 and 3, textile component 220 overlaps proximal shaft segment 106 at proximal end 107 of distal shaft segment 108 with a bonding sleeve 224 positioned to surround the overlap. Bonding sleeve 224 is thermally bonded to proximal shaft segment 106 to secure textile component 220 therebetween. The proximal end of textile component 220 includes perforations 228 regularly spaced about a circumference to allow segments of bonding sleeve 224 and proximal shaft segment 106 to thermally join therethrough during the thermal bonding process. In embodiments hereof, bonding sleeve 224 may be formed from thin-walled tubing made of PEBAX® material, polyamide, nylon or a nylon blend. In another embodiment, bonding sleeve 224 may be omitted and proximal shaft segment 106 may be attached to textile component 220 with an adhesive, such as cyanoacrylate, which may also be applied within perforations 228 to aid in adhesive attachment of textile component 220 and proximal shaft segment 106.

In FIGS. 2 and 3 a distal end 227 of a tubular middle member 226 is shown positioned within a proximal end of tubular textile component 220. In another embodiment, distal end 227 of tubular middle member 226 may be positioned proximal of tubular textile component 220 such that a proximal end of a stent-graft constrained by textile component 220 resides within a distal end 105 of proximal shaft segment 106. A proximal end (not shown) of middle member 226 is anchored within handle 110 to fix a longitudinal position of middle member 226 within outer tubular shaft 104. Outer tubular shaft 104, viz., proximal and distal segments 106, 108, is retractable relative to middle member 226 and guidewire shaft 114 in the direction of the retraction arrow shown in FIG. 3.

Delivery system 100 is well suited for being introduced into a femoral artery and advanced through an iliac artery into the aorta for repair of an aortic aneurysm. In FIG. 4 delivery system 100 is shown, after having been tracked through the vasculature over guidewire 440, with distal portion 102 bridging an aneurysm, such as an aneurysm in the thoracic aorta. Within distal portion 102, a compressed self-expanding stent-graft 450 is shown constrained by textile component 220 and longitudinally disposed between middle member 226 and tip component 112. In an embodiment, stent-graft 450 is a self-expanding, nitinol/DACRON® stent-graft system designed for endovascular exclusion, such as for Thoracic Aortic Aneurysms (TAA), and may be the TALENT® stent-graft manufactured and sold by Medtronic, Inc of Minneapolis, Minn.

During deployment of stent-graft 450 at the treatment site, middle member 226 acts as a proximal stop to prevent proximal migration of stent-graft 450 during retraction of outer tubular shaft 104. More particularly with reference to FIG. 5, middle member 226 provides an opposing force against a proximal end 452 of stent-graft 450 to equalize the force imparted by textile component 220 as textile component 220 slides or slightly drags across stent-graft 450 during retraction. Hub component 222, which radial supports the distal end of textile component 220, slides over the bare metal anchors or annular spring-like supports of stent-graft 450 to ease proximal retraction of textile component 220 there over. Accordingly as textile component 220 is retracted, stent-graft 450 is held in its longitudinal position to properly deploy/release across the aneurysm such that proximal and distal ends 452, 454 of stent-graft 450 expand into apposition with the vessel wall and a body portion of stent-graft 450 bridges/closes-off the aneurysm.

Flexible textile component 220 of outer tubular shaft 104 as described herein remains in its original, low-profile form as delivery system 100 is introduced into the patient and tracked through the vasculature to the desired delivery site. Textile component 220 imparts flexibility to distal shaft segment 108 to reduce the potential for patient trauma and operator burden during the interventional procedure.

While various embodiments have been described above, it should be understood that they have been presented by way of illustration and example only, and not limitation. It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment.

What is claimed is:
1. A stent-graft delivery system comprising:
an outer tubular shaft having a proximal shaft segment attached to a distal shaft segment having a tubular textile component consisting of a fabric or cloth for flexibility, a distal end of the proximal shaft segment being attached to a proximal end of the tubular textile component by an attachment mechanism, wherein the proximal shaft segment is of a polymeric tubing that has a substantially greater resistance to bending than the tubular textile component and wherein the tubular textile component is non-compliant;
an inner shaft that extends through an entire length of the outer tubular shaft;
a distal tip component attached to the inner shaft,
wherein a hub component is attached to a distal segment of the tubular textile component to provide radial support thereto, the hub component having an inner diameter that is sized to receive a proximal end of the distal tip component, and
wherein the hub component includes a polymeric inner support tube and a polymeric outer support tube between which the distal segment of the tubular textile component is disposed; and
a self-expanding stent-graft positioned around a distal portion of the inner shaft and constrained by the tubular textile component in a compressed delivery configuration, wherein retraction of the outer tubular shaft proxi- mally slides the tubular textile component over the stent-graft to expose and deploy the stent-graft.

2. The delivery system of claim 1, wherein the attachment mechanism is an adhesive.

3. The delivery system of claim 2, wherein the tubular textile component is made from a woven fabric of strands of a biocompatible polymeric material.

4. The delivery system of claim 2, wherein a circumference of the proximal end of the tubular textile component includes regularly spaced perforations that receive the adhesive for attaching the tubular textile component to the proximal shaft segment distal end.

5. The delivery system of claim 1, wherein a circumference of the distal end of the tubular textile component includes regularly spaced perforations that receive an adhesive for attaching the tubular textile component between the inner and outer support tubes of the hub component.

6. The delivery system of claim 1, further comprising:
a tubular middle member disposed within the outer tubular shaft and having a distal end proximate an end of the stent-graft held within the tubular textile component, wherein the outer tubular shaft is longitudinally slidable relative to the middle member, the inner shaft and the distal tip component to deploy the stent-graft.

7. The delivery system of claim 6, wherein the middle member acts as a proximal stop to prevent proximal migration of the stent-graft with the tubular textile component during retraction of the outer tubular shaft.

8. A stent-graft delivery system comprising:
an outer tubular shaft having a proximal shaft segment and a distal shaft segment having a tubular textile component consisting of a fabric or cloth, a distal end of the proximal shaft segment being thermally bonded to a proximal end of the tubular textile component, wherein the proximal shaft segment is of a polymeric tubing that has a substantially greater resistance to bending than the tubular textile component and the outer tubular shaft having a substantially constant outer diameter from a proximal end to a distal end thereof;
an inner shaft that extends through an entire length of the outer tubular shaft;
a distal tip component attached to the inner shaft,
wherein a hub component is attached to a distal segment of the tubular textile component to provide radial support thereto, the hub component having an inner diameter that is sized to receive a proximal end of the distal tip component, and
wherein the hub component includes a polymeric inner support tube and a polymeric outer support tube between which the distal segment of the tubular textile component is disposed; and
a self-expanding stent-graft positioned around a distal portion of the inner shaft and constrained by the tubular textile component in a compressed delivery configuration, wherein retraction of the outer tubular shaft proximally slides the tubular textile component over the stent-graft to expose and deploy the stent-graft.

9. The delivery system of claim 8, wherein the tubular textile component is made from a woven fabric of strands of a biocompatible polymeric material.

10. The delivery system of claim 8, wherein a bonding sleeve surrounds a portion of the tubular textile component proximal end which overlaps the proximal shaft segment distal end and a circumference of the proximal end of the tubular textile component includes regularly spaced perforations that allow the bonding sleeve and the proximal shaft segment distal end to join therethrough when thermally bonded.

11. The delivery system of claim 8, further comprising:
a tubular middle member coaxially disposed between the outer tubular shaft and the inner shaft and having a distal end proximate an end of the stent-graft held within the tubular textile component, wherein the middle member acts as a proximal stop to prevent proximal migration of the stent-graft with the tubular textile component during retraction of the outer tubular shaft.

12. The delivery system of claim 8, wherein a circumference of the distal end of the tubular textile component includes regularly spaced perforations that allow the inner support tube to join with the outer support tube therethrough when thermally bonded.

* * * * *